United States Patent [19]

Yuhki et al.

[11] Patent Number: 4,956,146
[45] Date of Patent: Sep. 11, 1990

[54] DRY ANALYTICAL ELEMENT AND PROCESS FOR PRODUCING THE SAME

[75] Inventors: Hirokazu Yuhki; Kazuhiko Fujiwara; Hiroshi Ohnishi; Fuminori Arai, all of Saitama, Japan

[73] Assignee: Fuji Photo Film Co., Ltd., Kanagawa, Japan

[21] Appl. No.: 321,978

[22] Filed: Mar. 10, 1989

[30] Foreign Application Priority Data

Mar. 14, 1988 [JP] Japan .................................. 63-59921

[51] Int. Cl.$^5$ ...................... G01N 33/00; G01N 21/77; C12Q 1/28
[52] U.S. Cl. ......................................... 422/56; 422/57; 435/28; 435/805; 436/135; 436/904; 436/169; 436/170
[58] Field of Search .................... 422/56, 57; 436/169, 436/170, 66, 135, 136, 904; 435/28, 805

[56] References Cited

U.S. PATENT DOCUMENTS

| | | | |
|---|---|---|---|
| 3,992,158 | 11/1976 | Przybylowicz et al. | 422/57 |
| 4,089,747 | 5/1978 | Bruschi | 436/95 |
| 4,260,393 | 4/1981 | Gibson | 435/28 |
| 4,356,149 | 10/1982 | Kitajima et al. | 435/805 |
| 4,567,024 | 1/1986 | Koyama et al. | 435/805 |
| 4,615,982 | 10/1986 | Lawrence | 436/904 |
| 4,665,023 | 5/1987 | Deneke et al. | 436/135 |
| 4,721,670 | 1/1988 | Osada et al. | 436/135 |
| 4,732,736 | 3/1988 | Kobayashi et al. | 435/28 |
| 4,780,411 | 10/1988 | Piejko et al. | 435/805 |
| 4,812,399 | 3/1989 | Mauck et al. | 422/56 |

FOREIGN PATENT DOCUMENTS

| | | |
|---|---|---|
| 0124878 | 3/1984 | European Pat. Off. . |
| 0122641 | 4/1984 | European Pat. Off. . |
| 0165588 | 12/1985 | European Pat. Off. ............. 435/28 |
| 0285095 | 3/1988 | European Pat. Off. . |
| 0308236 | 3/1989 | European Pat. Off. ............. 435/28 |
| 89104449 | 7/1989 | European Pat. Off. . |

Primary Examiner—Robert J. Warden
Assistant Examiner—Thalia P. Vassilatos
Attorney, Agent, or Firm—McAulay Fisher Nissen & Goldberg

[57] ABSTRACT

A dry analytical element for use in detecting a specific component contained in a liquid, which element comprises one or more water permeable layers provided on a water impermeable support, at least one layer of the water-permeable layers containing a composition capable of interacting with said specific component contained in said liquid. The composition contains a leuco dye and a dispersion containing said leuco dye is incorporated in the water-permeable layer, which is formed by dissolving the leuco dye in a hydrophobic solvent containing an aliphatic higher alcohol and dispersing the resulting solution in a hydrophilic medium. The leuco dye has the formula:

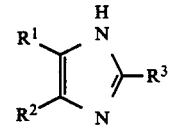

[I]

where $R^1$ represents an unsubstituted or substituted aryl group, $R^2$ represents an unsubstituted or substituted alkyl group, and $R^3$ represents an unsubstituted or substituted aryl group. A process for producing said dry analytical element is also disclosed.

20 Claims, No Drawings

DRY ANALYTICAL ELEMENT AND PROCESS FOR PRODUCING THE SAME

FIELD OF THE INVENTION

This invention relates to a dry analytical element suitable for use in detecting and determining specific components in liquids, and more particularly to a dry analytical element suitable for use in detecting specific components capable of forming hydrogen peroxide or participating in a hydrogen peroxide forming reaction.

BACKGROUND OF THE INVENTION

There are known many analytical methods in which specific components are determined by detecting hydrogen peroxide which is formed by the reaction of said specific components. Among them, there is a method using leuco dyes having an imidazole nucleus.

One mol of a dye is formed from one mol of hydrogen peroxide interacting with one mol of a leuco dye and the dye has a high molecular extinction coefficient so that they have the advantage in that their detection sensitivity is high. On the other hand, they have a disadvantage in that it is difficult to make an accurate measurement since dyes formed by the leuco dyes fade rapidly after color formation.

It was found that the fading of the dye produced by the leuco dye can be substantially prevented by dissolving the leuco dye in a hydrophobic solvent, dispersing the solution in a hydrophilic medium and incorporating the dispersion in a water-permeable layer (see, JP-A-63-247657 corresponding to EP 285095A2) (The term "JP-A" as used herein means an "unexamined published Japanese patent application"). However, when a leuco dye is dissolved in a hydrophobic solvent and then dispersed in a hydrophilic medium, the color forming rate is reduced.

Further, the mean particle size of the dispersion is increased, when a dispersion of a leuco dye dissolved in a hydrophobic solvent is stored at 40° C. for two or three hours or at 5° C. for about one week even if a conventional anionic surfactant is used. Namely, the dispersion is unstable.

SUMMARY OF THE INVENTION

A first object of the present invention is to provide a dry analytical element which is substantially free from the lowering in analytical accuracy due to the fading of the dye formed from the leuco dye without lowering in the color forming rate, which element is thus suitable for use in determining specific components in liquids by detecting the hydrogen peroxide formed by the reaction of said specific components.

A second object of the present invention is to provide a dry analytical element wherein a solution of a leuco dye dissolved in a hydrophobic solvent is stably dispersed in a hydrophilic medium.

The above objects of the present invention may be achieved, separately or simultaneously, by a dry analytical element which contains a leuco dye capable of interacting with hydrogen peroxide to form a dye, said leuco dye having formula [I]:

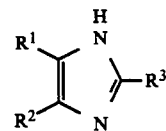

wherein $R^1$ represents an unsubstituted or substituted aryl group, $R^2$ represents an unsubstituted or substituted alkyl group, and $R^3$ represents an unsubstituted or substituted aryl group, wherein a dispersion of the leuco dye is obtained by dissolving the leuco dye and an aliphatic higher alcohol in a hydrophobic solvent and despersing the resulting solution in a hydrophilic medium.

DESCRIPTION OF THE PREFERRED EMBODIMENT

Preferably, in the formula [I], $R^1$ is an aryl group, e.g., phenyl, which may be optionally substituted. Examples of substituent groups include hydroxyl group, alkoxy group, amino group, alkylamino group, dialkylamino group, and the like. Among them, a dialkylamino group, such as, dimethylamino or diethylamino group is preferred.

$R^2$ is an alkyl group, e.g., methyl, ethyl, which may be optionally substituted. Examples of substituent groups include phenyl group, phenoxy group, 4-dimethylaminophenyl group, and the like.

$R^3$ is an aryl group which may be optionally substituted. Examples of substituent groups include hydroxyl group, an alkoxy group having preferably 1 to 4 carbon atoms, and the like.

Typical examples of the aryl group represented by $R^1$ include 4-dimethylamino-phenyl group and 4-diethylaminophenyl group. Typical examples of the alkyl group represented by $R^2$ include the benzyl group and phenethyl group. The phenethyl group is preferred. Typical examples of the aryl group represented by $R^3$ include 4-hydroxyphenyl group and 3,5-dimethoxy-4-hydroxyphenyl group.

The synthesis method of the above-described leuco dyes is disclosed in JP-A 59-193352.

The aforementioned second object of the present invention has been achieved by providing a process for producing a dry analytical element comprising dissolving a leuco dye having the following formula [II]:

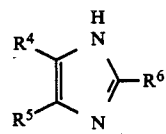

wherein $R^4$ represents an unsubstituted or substituted aryl group, $R^5$ represents an unsubstituted or substituted aryl group or an unsubstituted or substituted alkyl group, and $R^6$ represents an unsubstituted or substituted aryl group; and an aliphatic higher alcohol in a hydrophobic solvent, dispersing the resulting solution in a hydrophilic medium and then incorporating the dispersion in a water permeable layer.

In formula [II], the aryl group (e.g., phenyl group) represented by $R^4$ and $R^5$ may be optionally substituted. Examples of substituent groups include a hydroxyl group, an alkoxy group, amino group, an alkylamino group, a dialkylamino group, etc. Among them, a dialkylamino group, such as a dimethylamino group or diethylamino group is preferred. $R^4$ and $R^5$ may be the same or different aryl group, but are preferably the same aryl groups from the viewpoint of synthesis.

Examples of the alkyl group represented by $R^5$ include a methyl group, ethyl group, etc. The alkyl group may be optionally substituted. Examples of substituent groups include a phenyl group, phenoxy group, 4-dimethylaminophenyl group, and the like.

$R^6$ is an aryl group which may be optionally substituted. Examples of substituent groups include the hydroxyl group, an alkoxy group having preferably 1 to 4 carbon atoms, and the like.

Typical examples of the aryl group represented by $R^4$ and $R^5$ include 4-diethylaminophenyl group and 4-dimethylaminophenyl group. Typical examples of the alkyl group represented by $R^5$ include the benzyl group and phenethyl group. The phenethyl group is preferred. Typical examples of the aryl group represented by $R^6$ include the 4-hydroxyphenyl group and 3,5-dimethoxy-4-hydroxyphenyl group.

Methods for synthesizing the above leuco dyes are disclosed in U.S. Pat. No. 4,089,747 and EP 0122641A2.

Dry analytical elements suitable for use in determining biochemical substances contained in body fluid are known and described in, for examples, JP-A-49-53888 (corresponding to U.S. Pat. No. 3,992,158), JP-A-55-164356 (corresponding to U.S. Pat. No. 4,292,272) and JP-A-59-102388. Generally, analysis by using the dry analytical element is carried out such that a substance to be analyzed is determined by photometrically measuring the amount of the reaction product from the reaction between the substance to be analyzed and a reagent contained in the analytical element or the amount of unreacted component by spectrophotometry, such as color formation, color change, fluorometry, emission spectrophotometry, etc. By the use of the dry analytical element, a specific component such as a biochemically active substance in body fluid can be analyzed simply and rapidly with high accuracy.

The analytical element of the present invention has at least one water-permeable layers, and preferably, at least two water-permeable layers. It is desirable that the analytical element has a water-impermeable support, though no support may be used. It is preferred that the support is light-transmissive.

The leuco dye may be formed by an interaction between a desired specific component in a sample solution and a composition in the analytical element, or may be formed by an interaction between the components in the element as a result of the activity of the specific component, for example, by the catalytic action thereof. The interaction may comprise a single reaction, or a plurality of reactions. The term "interaction" as used herein refers to chemical activity, catalytic activity as in the formation of enzyme substrate composite material, immunogen activity in the antigen-antibody reaction and all chemical or physical interactions capable of forming a detectable dye at a concentration such that the concentration of the dye reflects, directly or indirectly, the presence of a specific substance to be analyzed.

The above-described interacting composition is determined according to the analytical reaction chosen. When enzyme activity in a sample solution is to be measured, the interacting composition must contain a substrate for the enzyme. When the substance to be analyzed in a sample solution is a substrate for an enzyme, the analysis can be carried out by incorporating an enzymatic material active on said substrate in the interacting composition.

Interacting compositions useful for the present invention include substances having oxidase activity. An enzyme, for example, a substance having oxidase activity, such as, glucose oxidase, glycerol oxidase, cholesterol oxidase or pyruvic oxidase may be incorporated in the reagent layer or liquid-spreading layer of the analytical element to analyze components which are substrates for these enzymes. These substrates can be applied to the analysis of an enzyme, a substrate, an antigen and an antibody which form from enzyme reactions or immunity reactions (antigen-antibody reaction).

The entirety of a reagent composition may be incorporated in one water-permeable layer. Alternately, the reagent composition may be incorporated into two or more water-permeable layers. For example, three reagent layers may be provided and a composition forming an intermediate by the reaction between the component to be analyzed and the reagent, is incorporated in the third reagent layer which is most distant from the support. A composition producing hydrogen peroxide by the reaction between said composition and said intermediate, is incorporated in the second layer. A dispersion containing a leuco dye is incorporated in the first reagent layer which is nearest to the support.

Alternatively, two reagent layers may be provided. A composition producing hydrogen peroxide by the reaction between the component to be analyzed and the reagent is incorporated in the second reagent layer which is most distant from the support. A dispersion containing a leuco dye is incorporated in the first reagent layer nearest to the support.

If desired, a composition yielding an intermediate by the reaction between a component to be analyzed and a reagent may be incorporated in the second reagent layer which is most distant from the support. A leuco dye dispersion and a composition producing hydrogen peroxide by a reaction thereof with said intermediate may be incorporated in the first reagent layer which is nearest to the support.

The entirety of the reagent composition may be incorporated in a substantially uniform layer containing a hydrophilic polymer as a binder. A part thereof may be incorporated in a porous layer. If desired, all or a portion thereof may be incorporated in any layer among a plurality of porous layers as described JP-A-62-138756, JP-A-62-138757 and JP A-62-138758.

A useful method for incorporating at least a portion of the reagent composition in the porous layer is provided by bonding a porous spreading layer previously impregnated or coated with an appropriate solution or dispersion of the reagent composition to another water-permeable layer, such as a substantially uniform layer containing a hydrophilic polymer as a binder, by a method as described in JP-A-55-164356. Alternatively, after a porous layer is bonded to the surface of another water-permeable layer (e.g., an undercoating layer, adhesive layer, water absorption layer, or a first reagent layer) by a method described in said JP-A-55-164356, said porous layer is coated with a solution or dispersion of the reagent composition. The impregnation or coating of the porous layer with the solution or dispersion can be made by conventional methods. For example, coating may be carried out by dip coating, extrusion coating, doctor coating, hopper coating, curtain coating, etc.

Typical examples of the leuco dyes suitable for use in the present invention include the following compounds.

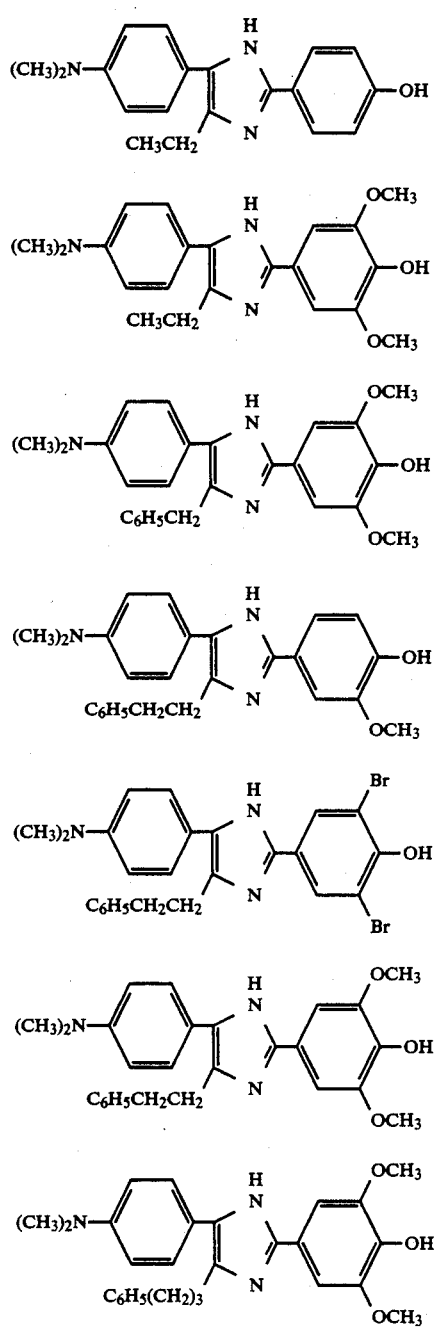

The leuco dye having the formula [I] or [II] is contained in the form of a dispersion in at least one water-permeable layer of the dry analytical element. The water-permeable layer may be a porous layer, but is preferably a non-porous layer containing a hydrophilic polymer as a binder. Examples of the hydrophilic polymer include gelatin, gelatin derivatives, e.g., phthalated gelatin, cellulose derivatives, e.g., hydroxyethyl cellulose, agarose, acrylamide polymers, methacrylamide polymers and copolymers of acrylamide or methacrylamide with various vinyl monomers.

Conventional hydrophobic solvents, conventional hydrophilic media and conventional dispersing methods can be used.

The dispersion of the solution of the leuco dye dissolved in the hydrophobic solvent is contained in the continuous phase of the hydrophilic polymer. Hydrophobic solvents conventionally used in multi-layer gelatin/silver halide color photographic materials can be used. For example, solvents described in U.S. Pat. No. 2,322,027 can be used. Examples of the solvents include phthalic diesters, such as, dibutyl phthalate, dicyclohexyl phthalate, di-2-ethylhexyl phthalate and decyl phthalate; phosphoric esters, such as, triphenyl phosphate, tricresyl phosphate, 2-ethylhexyl diphenyl phosphate, tricyclohexyl phosphate and tri-2-ethylhexyl phosphate; benzoic esters, such as, 2-ethylhexyl benzoate; amides, such as, N,N-diethyllaurylamide and N-tetradecyl-pyrrolidone; phenols, such as 2,4-di-t-amylphenol; fatty acid esters, such as trioctyl citrate; hydrocarbons, such as paraffin; and halogenated hydrocarbons, such as chlorinated paraffin. These solvents are generally high-boiling solvents.

In dissolving the leuco dye in a high-boiling solvent, there may be used a high-boiling solvent alone or together with a low-boiling solvent. Alternatively, the leuco dye is dissolved in a low-boiling solvent and then may be mixed with a high-boiling solvent. As the low-boiling solvent, organic solvents having a boiling point of from 50° to 160° C. can be used. Examples of the organic solvents include fatty acid esters, such as ethyl acetate, butyl acetate and 2-ethoxyethyl acetate; ketones, such as methyl ethyl ketone; and amides, such as dimethylformamide.

A feature of the present invention resides in the addition of an aliphatic higher alcohol in addition to said high-boiling solvent. The aliphatic higher alcohols which can be used in the present invention are straight-chain or branched monohydric alcohols having from 12 to 30 carbon atoms, preferably 14 to 20 carbon atoms. Primary alcohols are preferred, though secondary and tertiary alcohols can be used. Typical examples include cetyl alcohol and stearyl alcohol. The alcohols used in the present invention may have unsaturated bonds.

The aliphatic higher alcohol is used in an amount of 0.1 to 20% by weight, preferably 6 to 15% by weight based on the amount of the high-boiling solvent. The leuco dye is dissolved in a hydrophobic solvent containing the aliphatic higher alcohol and the resulting solution may be dispersed in an aqueous solution of a hydrophilic medium. Alternatively, after the leuco dye is dissolved in the hydrophobic solvent, the aliphatic higher alcohol is added thereto and the resulting solution may be dispersed in an aqueous solution of the hydrophilic medium.

The solution of the leuco dye can be dispersed in an aqueous solution of a hydrophilic polymer by various known dispersing methods, particularly the dispersing method used in preparing oil-in-water type dispersions (e.g., methods described in JP-A-55-129136, JP-A-59-203632 and JP-A-62-86363). In a preferred method, after adding water (optionally containing an emulsifying agent) to a solution of a leuco dye in an organic solvent (optionally containing an emulsification aid) to form a water-in-oil type emulsion, the phase inversion of the W/O emulsion to an O/W emulsion is carried out and an appropriate binder (hydrophilic colloid) is then added thereto (JP-A-55-129136, JP-A-59-203632). It is preferred to use a surfactant as an emulsification aid in carrying out the dispersion.

Examples of the surfactants which can be used as an emulsification aid include alkylene oxide compounds, e.g., polyethylene glycol (hereinafter abbreviated to PEG), condensates of PEG with polypropylene glycol, PEG alkyl ethers, PEG alkylphenyl ethers, PEG alkyl esters, PEG sorbitan esters, PEG alkylamines, PEG amides), glycidol derivatives, e.g., alkenylsuccinic acid polyglycidols, alkylphenol polyglycidols, esters of polyhydric alcohols with fatty acids, sucrose alkyl esters, sucrose urethanes, sucrose ethers, saponin (steroid), saponin (triterpenoid), alkylcarboxylic acids, alkylsulfonic acids, alkyl sulfosuccinates, e.g., di-2-ethylhexyl sodium sulfosuccinate, alkylbenzenesulfonic acids, e.g., sodium dodecylbenzenesulfonate, alkylnaphthalenesulfonic acids, alkylsulfuric esters, alkylphosphoric esters, alkylphenoxypolyethoxyalkylsulfonic acids, polyoxyethylenealkykl phosphates, amino acids, aminoalkylsulfonic acids, aminoalkylsulfuric esters, aminoalkyl phosphates, alkylbetaines, amineimides, amine oxides, alkylamine salts, aliphatic quaternary ammonium salts, aromatic quaternary ammonium salts, heterocyclic quaternary ammonium salts, e.g., pyridinium salts, imidazolium salts, aliphatic sulfonium salts, and aliphatic phosphonium slats.

The ratio of the hydrophobic solvent to the hydrophilic medium varies depending on the content of the leuco dye, dispersion stability, and the desired physical properties of the dispersion Generally, the range of hydrophobic solvent to hydrophobic medium is in the range of from 8:1 to 1:10, preferably from 3:1 to 1:4.

The hydrophobic solution containing the leuco dye can be dispersed in a hydrophilic medium solution by using a high-speed stirring dispersion mixer having a high shearing force, a dispersion mixer utilizing ultrasonic energy and the like. Examples of the dispersion mixers include a colloid mill, homogenizer, capillary tube type emulsifier, ultrasonic emulsifier using an electromagnetic distortion element and an emulsifier using a Bollman pipe. Since the impeller of the dispersion mixers, which gives the shearing force, is revolved at a speed of 500 to 20000 revolutions per minute in the solution, they are known under the trade names of the Dissolver, Polytrone, Homomixer, Homoblender, Kedy mill, Jet Agitator, and the like.

The layer of the leuco dye dispersion (or the hydrophilic medium containing the leuco dye dispersion) can be provided on a water impermeable support by using a method wherein a liquid comprising the dispersion is coated on the surface of the support and then dried. Coating can be conducted by means of dip coating, extrusion coating, doctor coating, hopper coating, curtain coating, and the like.

The present invention can be applied to known various dry analytical elements. The analytical element may be composed of a multi-layer structure consisting of a porous layer and reagent layer as well as those having a support, a spreading layer, a detecting layer, a light-blocking layer, an adhesive layer, a filter layer, a water absorbing layer, a subbing layer and other layers. Such analytical elements are disclosed in U.S. Pat. Nos. 3,992,158 and 4,042,335 and JP-A-55-164356. (corresponding to U.S. Pat. No. 4,292,272).

When a water-impermeable light-transmissive support is used, the dry analytical element of the present invention may have any of the following structures:

(1) A structure where the reagent layer is provided on the support; and the spreading layer is provided on the reagent layer.

(2) A structure where the detection layer, the reagent layer and then the spreading layer, in this order, are provided on the support.

(3) A structure where the reagent layer, the light reflecting layer and then the spreading layer, in this order, are provide on the support.

(4) A structure where the detecting layer, the reagent layer, the light reflecting layer and then the spreading layer are provided on the support.

(5) A structure where the detecting layer, the light reflecting layer, the reagent layer and then the spreading layer, in this order, are provided on the support.

(6) A structure where the second reagent layer, the light reflecting layer, the first reagent layer and then the spreading layer, in this, order are provided on the support.

(7) A structure where the detecting layer, the second reagent layer, the light reflecting layer and then the spreading layer, in this order, are provided on the support.

The reagent layer in the above structures (1) to (5) may be composed of a plurality of different layers. The water absorbing layer may be provided between the support and the reagent layer or the detecting layer. In structures (1) to (3) and (6), the filter layer may be provided between the reagent layer and the detecting layer or the spreading layer. In structures (3) to (7), a filter layer may be provided: between the light reflecting layer and the detecting layer, the reagent layer and the spreading layer; or between the reagent layer and the detecting layer; or between the reagent layer and the spreading layer. When the reagent layer is composed of two or more layers, a filter layer may be provided between the reagent layers.

The present invention can be used for the determination of various analyzable substances in whole blood, plasma or serum. The present invention is applicable for the determination of metabolic materials, such as, glucose, cholesterol, uric acid, glycerol, triglyceride, uric acid and bilirubin as well as for the measurement of enzyme activity of creatine kinase, transaminase, e.g., alanine aminotransferase, or aspartate aminotransferase, or hydrolase, e.g., amylase, acid phosphatase, or alkaline phosphatase.

The present invention can also be used for immunity analysis using specific antibody or antigen.

As the reagent layer of the dry analytical element of the present invention, a substantially uniform layer containing the hydrophilic polymer as a binder as well as porous layers as described in JP-A-58-70163, JP-A-61-4959 and JP-A Nos. 62-116258, 62-138756, 62-138757 and 62-138758 can be used.

The reagent layer containing the leuco dye may contain the leuco dye dispersion phase as well as enzymes, coenzymes, substrates for enzymes, oxidizing agents, buffering agent, and the like Examples of the buffering agents which can be incorporated in the reagent layer of the analytical element of the present invention include carbonates, borates, phosphates and Good's buffering agent described in biochemistry, Vol. 5, No. 2, PP 467-477 (1966). These buffering agents can be properly chosen by referring to Fundamental Experimental Method of Protein Enzyme (written by Takeichi Oshio et al., published by Nanedo, 1981, written in Japanese) and the aforementioned Biochemistry, Vol. 5.

When the porous layer is utilized as the spreading layer, it is desirable that the layer has a liquid-metering action. The term "liquid-metering action" as used herein refers to an action capable of spreading a liquid sample at a substantially constant rate per unit area over the whole surface of the layer without causing the uneven distribution of components contained in the liquid sample, when the liquid sample is deposited on the surface of said porous layer.

Examples of materials which can be used for the spreading layer and other porous layers of the present invention include filter paper, nonwoven fabric, woven fabric, e.g., plain weave fabric, knitted fabric, e.g., tricot weave, glass fiber and filter cloth. Among them, woven fabric and knitted fabric are preferred as the materials for the spreading layer. These fabrics, may be treated with glow discharge as described in JP-A-57-66359. The spreading layer may contain hydrophilic high-molecular material or surfactants as described in JP-A-Nos. 60-222770, 63-219397, 63-112999 and 62-182652 to adjust the spreading area, spreading rate, and other properties.

An adhesive layer for use in laminating the porous layer by bonding may be provided on a layer, such as, the reagent layer, the light reflecting layer, the filter layer, the water absorbing layer or the detecting layer. The adhesive layer comprises a hydrophilic polymer, such as, gelatin, gelatin derivative, polyacylamide or starch so as to bond the porous layer when the adhesive layer is swollen with water.

The analytical element of the present invention may have a light reflecting layer. For example, a light reflecting layer may be provided between the reagent layer and the detecting layer or between the reagent layer and the liquid spreading layer. The light reflecting layer functions to block the color of a liquid sample fed to the spreading layer by deposition, for example, the red color of hemoglobin, or the yellow color of bilirubin, particularly when the sample is whole blood, It also functions as a layer for reflecting light or a background layer, when the detectable change, i.e., color change, color formation, etc., produced in the detecting layer, the reagent layer, etc. is measured from the side of the light-transmissive support by reflection photometry. It is preferred that the light reflecting layer is a water-permeable layer composed of fine particles of a light reflecting material, e.g., titanium oxide, barium sulfate, and the like dispersed in a hydrophilic polymer as a binder. Preferred examples of the binder include gelatin, gelatin derivatives and polyacrylamide. If desired, a hardening agent may be added to a curable polymer, such as, gelatin. The spreading layer, the reagent layer, the detecting layer, and other layers of the analytical element may optionally contain particles, such as, titanium oxide particles.

The analytical element of the present invention may have a layer capable of removing substantially all of the blood corpuscles by filtration in addition to the spreading layer. Porous layers described in JP-A-58-70163, JP-A-61-4959, JP-A-Nos. 62-116258, 62-138756, 62-138757 and 62-138758 are suitable for use as such a layer in addition to the spreading layer.

After a whole blood sample is deposited, the analytical element can be subjected to incubation (heating) to thereby obtain test results quickly or accurately.

When a component to be analyzed exists, the component interacts with an interacting composition at a rate based on the concentration of the component to be analyzed in a sample. The rate of a dye formation or the amount of a dye formed in proportion to the concentration of the component to be analyzed, by placing the analytical element in an apparatus for detecting the dye. The dye can be detected by using conventional spectrophotometric measuring apparatuses, such as, apparatuses described in U.S. Pat. No. 4,584,275 and JP-A-No. 62-276440.

Now, the present invention will be illustrated in greater detail by reference to the following example and referential example.

REFERENTIAL EXAMPLE (1) Dispersion

| | |
|---|---|
| Leuco dye (*described below) acetate hydrochloride | 1.1 g |
| | 0.15 g |
| N,N-Diethyllaurylamide | 20 g |
| Stearyl alcohol | 2.5 g |

*2-(4-Hydroxy-3,5-dimethoxyphenyl)-4-[4-(dimethylamino)phenyl]-5-phenethylimidazole The above composition was placed in a tank equipped with an insulating jacket, a thermometer and a high-speed immpeller agitator and stirred at a low speed for 30 minutes, while keeping the composition at about 80° C., to thereby dissolve the solutes completely. Thereafter, the temperature was lowered to 50° C. While keeping the temperature at 50° C., 120 g of 20% gelatin solution containing 1.2 g of sodium dodecylbenzenesulfonate kept at 50° C. was added thereto and the mixture was mixed at a low speed for about one minute and then stirred at a high speed of 5700 rpm for 30 minutes. 290 cc of 12% gelatin solution were added thereto to dilute it and the mixture was stirred at a low speed for 10 minutes to obtain an oil-in-water type emulsion, designated emulsion 1. The mean particle diameter thereof was 0.14 μ.

The same procedure for the preparation of the leuco dye solution was repeated except that the stearyl alcohol was omitted. An oil-in-water type emulsion designated as emulsion 2 was obtained. The mean particle diameter thereof was 0.21 μ.

(2) Stability of Emulsion

Emulsions 1 and 2 were stored at 40° C. for 3 hours, at 5° C. for one week, at 40° C. for 3 hours and then at 5° C. for one week. The changes in the mean particle diameter (μm) were measured. The results are shown in Table 1.

TABLE 1

| Sample | Storage at 40° C. | | Storage at 5° C. for | Storage at 5° C. for 1 week and at 40° C. for 3 hr |
|---|---|---|---|---|
| | 0 hr. particle diameter | 3 hrs. particle diameter | 1 week particle diameter | particle diameter |
| Ex. 1 | 0.140 | 0.146 | 0.150 | 0.150 |
| Comp. Ex. 1 | 0.210* | 0.330* | 0.300* | 0.400* |

*shows that coagulation occurred.

(3) Reproducibility of Color Formation

Each of the emulsions 1 and 2 prepared in the above item (1) was coated on the surface of a polyethylene terephthalate (PET) film of 180 μm in thickness in an amount to give a dry film of 20 μm in thickness. The coated layer was dried and further coated with a solution having the following composition in an amount to give a dry film of 7 μm in thickness. The resulting coat was dried to form a light reflecting layer.

| Water | 62 g |
|---|---|
| Alkalic-processed gelatin | 3.4 g |
| Rutile type titanium oxide | 34 g |
| Polyoxyethylene (n = 10) nonylphenyl ether | 0.3 g |

The light-reflecting layer obtained was coated with a gelatin solution and dried to provide an adhesive layer of 2 μm in thickness. Water at a rate of 30 g/m² was fed to the adhesive layer to swell it. Cloth knitted out of a polyethylene terephthalate spun yarn having 36 filaments and 50 denier with 40 gauges, was laminated onto the adhesive layer to provide a spreading layer. The spreading layer was coated with an ethyl alcohol solution of 2% hydroxypropyl cellulose in an amount of 200 cc/m² and dried.

The resulting element was cut into chips 15 mm square. Each was put into a mount as disclosed in JP-A -57-63452 to give a slide for the analysis of ferricyanide ion.

10 μl of a potassium ferricyanide solution (50 mg/dl) was deposited on the analytical slide. After 10 seconds, reflection optical density was measured at 640 nm. The measurement was repeated 10 times to examine the reproducibility of the color formation. The results are shown in Table 2. Figures (excluding the standard deviation) given in Table 2 are the reflection optical density.

TABLE 2

| Times | Emulsion 1 | Emulsion 2 |
|---|---|---|
| 1 | 0.643 | 0.621 |
| 2 | 0.643 | 0.672 |
| 3 | 0.632 | 0.628 |
| 4 | 0.642 | 0.688 |
| 5 | 0.637 | 0.612 |
| 6 | 0.643 | 0.652 |
| 7 | 0.648 | 0.649 |
| 8 | 0.649 | 0.682 |
| 9 | 0.639 | 0.662 |
| 10 | 0.647 | 0.652 |
| Average | 0.649 | 0.652 |
| Standard deviation | $4.14 \times 10^{-3}$ | $2.55 \times 10^{-2}$ |

It is apparent from Table 2 that the emulsion 1 is superior to the emulsion 2 in the repeating reproducibility of color formation.

EXAMPLE 1 AND COMPARATIVE EXAMPLE 1.1 Preparation of Leuco Dye Dispersion

Leuco dye solution
A leuco dye solution having the following composition A was prepared.

| 2-(4-Hydroxy-3,5-dimethoxyphenyl)-4-[4-(di-methylamino)phenyl]-5-phenethylimidazole (leuco dye)acetate | 4.4 g |
|---|---|
| 2-(4-Hydroxy-3,5-dimethoxyphenyl)-4-[4-(di-methylamino)phenyl]-5-phenethylimidazole hydrochloride | 0.6 |
| N,N-Diethyllaurylamide | 90 ml |
| Stearyl alcohol | 2.5 g |

Gelatin solution
A gelatin solution having the following composition B was prepared.

| Alkali-processed gelatin | 230 g |
|---|---|
| Water | 1400 g |
| Glucose oxidase | 40000 U |
| Peroxidase | 70000 U |
| Di-2-ethylhexyl sodium sulfosuccinate | 5 g |
| Bis[(vinylsulfonylmethylcarbonyl)-amino] methane | 2.3 g |

(U: international unit)

Preparation of emulsion
The solution A was added to the solution B while stirring the solution B at above 6000 r.m.p. in a TK autohomomixer (emulsifier manufactured by Tokushu Kikai Kogyo KK) for about 30 minutes to disperse the solution A in the solution B, thus preparing an emulsion.

1-2 Coating of Color Reagent Layer

The surface of a transparent polyethylene terephthalate (PET) film (support) having a gelatin undercoat and a thickness of 180 μm was coated with said emulsion at a rate of 150 g/m² and dried.

1-3 Light Reflecting Layer

A light reflecting layer (dry thickness of 7 μm) composed of the following components (coating weights given below) was provided on the color reagent layer by coating the reagent layer with an aqueous dispersion and drying it.

| Alkali-processed gelatin | 2.9 g/m² |
|---|---|
| Fine particle of rutile type titanium oxide | 13 g/m² |
| Nonylphenoxy polyglycide (average 10 glycidol unit content) | 400 mg/m² |

1-4 Adhesion Layer

An adhesion layer (dry thickness of 5 μm) composed of the following components (coating weights being given below) was provided on the light reflecting layer by coating the light reflecting layer with an aqueous solution and drying it.

| Alkali-treated gelatin | 6.7 g/m² |
|---|---|
| Nonylphenoxy polyglycide (average 10 glycidol unit content) | 600 mg/m² |

1-5 Spreading Layer

Water in an amount of 30 g/m² was fed to the surface of the adhesion layer to swell the surface of the adhesive layer almost uniformly. Tricot knitted cloth of 250 μm in thickness, woven out of a PET spun yarn having 50 denier with 36 gauges, was laminated onto the adhesion layer by slightly pressing it against the adhesion layer to provide a porous spreading layer.

The surface of the spreading layer was coated with a polymer-containing ethanol dispersion of the following components in an amount to give the following coating weights. The coated product was dried to prepare a multilayer analytical film for the quantitative analysis of glucose.

| Hydroxypropyl cellulose (methoxy group content) 28–30%, hydroxy-propoxy group content: | |
|---|---|
| 7–12%, viscosity of 2% aqueous solution at 20° C.: 50 cps) | 5 g/m² |
| Polyoxyethylene-p-nonylphenyl ether (average 40 oxyethylene units) | 500 mg/m² |

1-6 Analytical Slide

The resulting analytical film for the quantitative analysis of glucose was cut into chips 15 mm square. Each chip was put into a slide frame as described in JP-A-58-32350 to prepare a biochemical analytical slide for the determination of glucose.

COMPARATIVE EXAMPLE 1

The procedure of Example 1 was repeated except that stearyl alcohol in the solution A was omitted to prepare an analytical slide for glucose. 1 to 2 nearly circular patches per m² were observed on the color reagent layer of the analytical slide and 15 to 20 nearly circular patches per m² were observed on the light reflecting layer.

MEASUREMENT EXAMPLE 1

Glucose in amounts of 50 mg/dl, 100 mg/dl, 200 mg/dl and 300 mg/dl, respectively, were added to a 7% serum albumin solution to prepare a control serum. 10 μl of each of the four control serums was deposited on the spreading layer of each of the slides for the analysis of glucose prepared in Example 1 and Comparative Example 1. Each slide was incubated at 37° C. for 6 minutes. The optical color density of each analytical slide was measured from the side of the PET support by reflection photometry at a wavelength of 540 nm. The results are shown in Table 3.

TABLE 3

| Glucose concn. (mg/dl) | Example 1 | Comp. Ex. 1 |
|---|---|---|
| 0 | 0.162 | 0.165 |
| 50 | 0.435 | 0.438 |
| 100 | 0.695 | 0.729 |
| 200 | 1.105 | 1.100 |
| 300 | 1.420 | 1.432 |

It is apparent from Table 3 that the analytical slides of Example give the same analytical results as those of the analytical slides of Comp. Ex. 1.

An experiment using a control serum containing glucose in an amount of 100 mg/dl was repeated 10 times to evaluate the reproducibility. The measured reflection optical density was converted into concentration by using a calibration curve prepared from the above measurement to make a statistical calculation. The results are shown in Table 4.

TABLE 4

| Times | Example 1 | Comp. Ex. 1 |
|---|---|---|
| 1 | 100 | 95 |
| 2 | 101 | 103 |
| 3 | 101 | 108 |
| 4 | 103 | 102 |
| 5 | 99 | 103 |
| 6 | 102 | 105 |
| 7 | 101 | 110 |
| 8 | 100 | 102 |
| 9 | 102 | 108 |

TABLE 4-continued

| Times | Example 1 | Comp. Ex. 1 |
|---|---|---|
| 10 | 99 | 107 |
| Average | 101 | 104 |
| Standard deviation | 1.32 | 4.30 |

It is clear from Table 4 that the analytical element of Example 1 according to the- present invention is superior in reproducibility to that of Comparative Example, with a standard deviation smaller than the latter.

While the invention has been described in detail and with reference to specific embodiments thereof, it will be apparent to one skilled in the art that various changes and modifications can be made therein without departing from the spirit and scope thereof.

What is claimed is:

1. In a dry analytical element for use in detecting a specific component contained in a liquid, which element comprises one or more water-permeable layers provided on a water-impermeable support, at least one layer of the water-permeable layers containing a composition capable of interacting with said specific component to produce a leuco dye having formula [I]

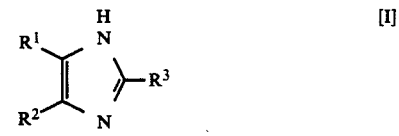

wherein $R^1$ represents an unsubstituted or substituted aryl group, $R^2$ represents an unsubstituted or substituted alkyl group, and $R^3$ represents an unsubstituted or substituted aryl group, the improvement wherein a dispersion containing said leuco dye is incorporated in said at least one layer containing said composition, said dispersion being formed by dissolving said leuco dye and an aliphatic higher alcohol in a hydrophobic solvent and dispersing the resulting solution in a hydrophilic medium.

2. A dry analytical element as in claim 1, wherein said dispersion is formed by dissolving said leuco dye in a hydrophobic solvent which contains an aliphatic higher alcohol and dispersing the resulting solution in a hydrophilic medium.

3. A dry analytical element as in claim 1, wherein at least two water permeable layers are provided on a water-impermeable support and at least one layer of said water-permeable layers contains said leuco dye.

4. The analytical element of claim 2, wherein the aliphatic higher alcohol is a straight chain or branched monohydric alcohol having from 12 to 30 carbon atoms.

5. The analytical element of claim 4, wherein the alcohol contains from 14 to 20 carbon atoms.

6. The analytical element of claim 4, wherein the alcohol is a primary alcohol.

7. The analytical element of claim 4, wherein the alcohol is cetyl or stearyl alcohol.

8. The analytical element of claim 1, wherein the amount of the alcohol is from 0.1 to 20% by weight based on the weight of the hydrophobic solvent.

9. The analytical element of claim 1, wherein the amount of the alcohol is from 6 to 15% by weight based on the weight of the hydrophobic solvent.

10. In a process for producing a dry analytical element for use in detecting a specific component in a liquid comprises one or more water-permeable layers provided on a water-impermeable support at least one of the water-permeable layers containing a composition capable of interacting with said specific component to produce a dye from a leuco dye having formula [II].

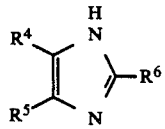

wherein $R^4$ represents an unsubstituted or substituted aryl group, $R^5$ represents an unsubstituted or substituted aryl group or an unsubstituted or substituted alkyl group, and $R^6$ represents an unsubstituted or substituted aryl group; the improvement which comprises dissolving said leuco dye and an aliphatic higher alcohol in a hydrophobic solvent, dispersing the resulting solution in a hydrophilic medium and incorporating the resulting dispersion in a water-permeable layer.

11. A process for producing a dry analytical element as in claim 10, wherein said leuco dye is dissolved in a hydrophobic solvent, an aliphatic higher alcohol is added thereto and the resulting solution is dispersed in a hydrophilic medium.

12. The process of claim 10, wherein the aliphatic higher alcohol is a straight chain or branched monohydric alcohol having from 12 to 30 carbon atoms.

13. The process of claim 12, wherein the alcohol contains from 14 to 20 carbon atoms.

14. The process of claim 12, wherein the alcohol is a primary alcohol.

15. The process of claim 12, wherein the alcohol is cetyl or stearyl alcohol.

16. The process of claim 10, wherein the amount of the alcohol is from 0.1 to 20% by weight based on the weight of the hydrophobic solvent.

17. The process of claim 10, wherein the amount of the alcohol is from 6 to 15% by weight based on the weight of the hydrophobic solvent.

18. The process of claim 10, wherein $R^5$ represents a substituted or unsubstituted alkyl group.

19. The process of claim 10, wherein $R^5$ represents a substituted alkyl group.

20. The process of claim 10, wherein $R^5$ represents a benzyl group or a phenethyl group.

* * * * *